US009775922B2

(12) United States Patent
Lee

(10) Patent No.: US 9,775,922 B2
(45) Date of Patent: Oct. 3, 2017

(54) STERILIZER FOR TOOTHBRUSHES, PUFFS FOR COSMETIC USE AND COSMETIC BRUSHES

(71) Applicant: Gil Soon Lee, Seoul (KR)

(72) Inventor: Gil Soon Lee, Seoul (KR)

( * ) Notice: Subject to any disclaimer, the term of this patent is extended or adjusted under 35 U.S.C. 154(b) by 0 days.

(21) Appl. No.: 15/145,675

(22) Filed: May 3, 2016

(65) Prior Publication Data

US 2017/0106108 A1    Apr. 20, 2017

(30) Foreign Application Priority Data

Oct. 16, 2015    (KR) .................. 20-2015-0006759 U

(51) Int. Cl.
*A61L 2/04*    (2006.01)

(52) U.S. Cl.
CPC ........................................ *A61L 2/04* (2013.01)

(58) Field of Classification Search
CPC ............ A61L 2/04; A45D 44/00; A45D 44/18
See application file for complete search history.

(56) References Cited

U.S. PATENT DOCUMENTS

2004/0025899 A1*  2/2004  Pinsky .................... A61L 2/10
                                                            132/310

FOREIGN PATENT DOCUMENTS

KR        10-0557780         2/2006
KR    10-2013-00995531       8/2013

* cited by examiner

*Primary Examiner* — Kevin Joyner
(74) *Attorney, Agent, or Firm* — Intellectual Property Law Group LLP

(57) ABSTRACT

A sterilizer for toothbrushes, puffs for cosmetic use and cosmetic brushes that dehydrates and sterilizes toothbrushes, puffs for cosmetic use and cosmetic brushes en bloc with ease and includes a housing 10, a cover 20 that is put on and removed from the housing from above, a dehydrating sterilizer member 30 that protrudes vertically upwards from the center of the bottom surface of the housing 10, a lower holder member 40 that is inserted in the housing 10 and has a insertion hole 44 through which the dehydrating sterilizer member 30 is inserted and hold cups 45 that accept toothbrushes and cosmetic brushes, an upper holder member 50 that is placed on the upper portion of the lower holder member 40 and a holder 60 that holds a puff for cosmetic use.

10 Claims, 7 Drawing Sheets

STERILIZER FOR TOOTHBRUSHES, PUFFS FOR COSMETIC USE AND COSMETIC BRUSHES

CROSS-REFERENCE TO RELATED APPLICATION

This application claims foreign priority under 35 U.S.C. §119 to Korean Utility Model Application no. 20-2015-0006759 filed in the Republic of Korea on Oct. 16, 2015, the entire contents of which are hereby incorporated by reference

BACKGROUND

1. Field of the Invention

The present invention related to a sterilizer for toothbrushes, puffs for cosmetic use and cosmetic brushes, and more particularly, a sterilizer for toothbrushes, puffs for cosmetic use and cosmetic brushes that may dehydrate, sterilize and cleanse toothbrushes, puffs for cosmetic use and cosmetic brushes en bloc with ease.

2. Background Art

It is reported that various microorganisms including bacteria proliferate in a toothbrush of daily use and the strands of a puff for cosmetic use and cosmetic brush a women uses such as puffs for cosmetic use and cosmetic brushes to apply foundation, makeup powder, etc. for wearing makeup base, makeup brushes to apply mascara on eyelashes, makeup brushes to apply lipsticks on the lips, etc.

A lot of prior arts have been provided for toothbrush sterilizers and cosmetic goods sterilizers, most of which are configured in a cumbersome way, thereby incurring high manufacturing costs and inconveniencing the user.

For example, most of the conventional toothbrush sterilizers include a toothbrush hanger that requires each of the brushes to be arranged in a specific direction whenever hanging the toothbrush while it is not convenient to disassemble the toothbrush hanger from the sterilizer for washing out.

In addition, most of the conventional cosmetic goods sterilizers include an exhaust fan as well as control circuit that controls the power ON/OFF feature of the sterilizer.

In many cases, a toothbrush is used in a bathroom for brushing the teeth while facial makeup is also performed on a dressing table in the proximity of a washbasin in a bathroom.

And yet, a device has not been developed that is troubleproof and low-priced and may dehydrate and sterilize toothbrushes that have no choice but to be infested with microorganisms in consequence of moisture that remains in the toothbrushes after use together with puffs for cosmetic use and cosmetic brushes in which bacteria proliferate when ignored after use or washed out and kept wet after a certain times of use.

PATENT LITERATURE (Patent Literature 1) Korean Patent Registration No. 10-0557780, Toothbrush sterilizer and dryer, as registered on Feb. 27, 2006

(Patent Literature 2) Korean Patent Publication No. 10-2013-0095531, Keepbox makeup set, as published on Aug. 28, 2013

SUMMARY OF THE INVENTION

Technical Problem

The present invention is directed to providing a troubleproof and low-priced sterilizer that may dehydrate and sterilize toothbrushes, puffs for cosmetic use and cosmetic brushes en bloc with ease.

The present invention is also directed to providing a sterilizer for toothbrushes, puffs for cosmetic use and cosmetic brushes from which an assembly member may be conveniently disassembled for cleansing.

Technical Solution

A sterilizer for toothbrushes, puffs for cosmetic use and cosmetic brushes according to the present disclosure includes a housing 10 that assumes the shape of a hexahedron and has a certain size of an opening in the upper portion of the housing and an internal storage space, a cover 20 that assumes the shape of a hexahedron and has an opening in the lower portion of the cover so that the cover is laid on and removed from the housing 10 from above and an internal storage space, a dehydrating sterilizer member 30 that assumes the shape of a hollow panel with a certain width and thickness and protrudes vertically upwards from the center of the bottom surface of the housing, a lower holder member 40 that includes a first lower holder member 41 that is a hexahedron, to be inserted into the housing 10, with the top surface is open and has a insertion tube 42 that extends upwards from the bottom surface of the first lower holder so that the dehydrating sterilizer member 30 is inserted from above to the bottom surface of the first lower holder and a second lower holder member 43, to be inserted into the first lower holder member 41, that has a insertion hole 44 in the center of the top surface to accept the dehydrating sterilizer member 30 and two or more hole cups 45 in either longitudinal side of the insertion hole 44 that are hollowed downwards to accept a toothbrush and cosmetic brush, an upper holder member 50 that is a plate the shape of which is identical to the top surface of the second lower holder member 43 and placed on the upper portion of the lower holder member 40, and a holder 60 that is inserted into a slit 35 formed in a side of the dehydrating sterilizer member 30, thereby holding a puff for cosmetic use.

The dehydrating sterilizer member 30 has on the surface a heat radiating plate 31 that has a certain width and spreads out on either side of the dehydrating sterilizer member 30 down to the bottom surface of the housing 10 while a plurality of negative ion emitting perforations 32 that penetrate at an identical interval the surface of the dehydrating sterilizer 30 and the heat radiating plate 31 so that the heat radiating plate 31 exerts heat and, simultaneously, the negative ion emitting perforations 32 that penetrate the heat radiating plate 31 discharge negative ions.

The first lower holder member 41 has in the internal wall, at a certain height, a protuberance and the second lower holder member 43 has in the rim of the top surface a stumbling block in order to assemble the second lower holder member 43 with the first lower holder member 41 while the second lower holder member 43 is mounted to and demounted from the first lower holder member 41.

The hole cup 45 of the second lower holder member 43 as a hollow cylinder having the top and bottom ends open has threads on the external surface of the lower end while a hole cup bottom lid member 46 as a hollow cylinder having the top end open has threads on the internal surface of the upper end so that the hole cup 45 and the hole cup bottom lid member 46 are fastened to and unfastened from each other.

The hole cup 45 and the hole cup bottom lid member 46 are disassembled from each other in order to wash out with ease the hole cup 45 and the hole cup bottom lid member 46.

The bottom surface of the hole cup bottom lid member 46 has a clearance between the bottom surface of the first lower holder member 41 and is slanted to a slight extent while the low end of the bottom surface of the hole cup bottom lid member 46 has a crack 47 to drain water.

The upper holder member 50 has in the center an upper insertion hole 51 into which the dehydrating sterilizer member 30 is inserted and in either longitudinal side two or more upper hole cups 52.

Both the lower holder member 40 and the upper holder member 50 may be pulled out of the housing 10 by simply and manually drawing them for cleansing with ease while the holder 60 may be pulled out of the slit 35 for cleansing with ease.

In addition, the cover 20 has two or more protrusions 21 in the internal surface so that the negative ions emitted via the negative ion emitting perforations 32 collide with the protrusions on the internal surface of the cover 20, thereby being dispersed in various directions.

Furthermore, the cover 20 may have two or more air vents 22 in the top surface.

Advantageous Effects of Invention

A sterilizer for toothbrushes, puffs for cosmetic use and cosmetic brushes according to the present invention is capable of drying and sterilizing toothbrushes that have no choice but to be infested with microorganisms in consequence of moisture that remains in the toothbrushes after use together with puffs for cosmetic use and cosmetic brushes in which bacteria proliferate when ignored after use or washed out and kept wet after a certain times of use.

In addition, the present invention provides a sterilizer for toothbrushes, puffs for cosmetic use and cosmetic brushes from which an assembly member that is vulnerable to scale may be conveniently disassembled for cleansing.

Furthermore, the present invention may provide a sterilizer for toothbrushes, puffs for cosmetic use and cosmetic brushes with lower manufacturing costs.

BRIEF DESCRIPTION OF THE DRAWINGS

FIG. 3A is a perspective view of a lower holder member and FIG. 3B is a top view of the lower holder member according to a sterilizer for toothbrushes, puffs for cosmetic use and cosmetic brushes according to the present invention while

DETAILED DESCRIPTION OF SPECIFIC EMBODIMENTS

Embodiments of a sterilizer for toothbrushes, puffs for cosmetic use and cosmetic brushes according to the present invention is described below in detail with reference to the drawings.

Figure 1:
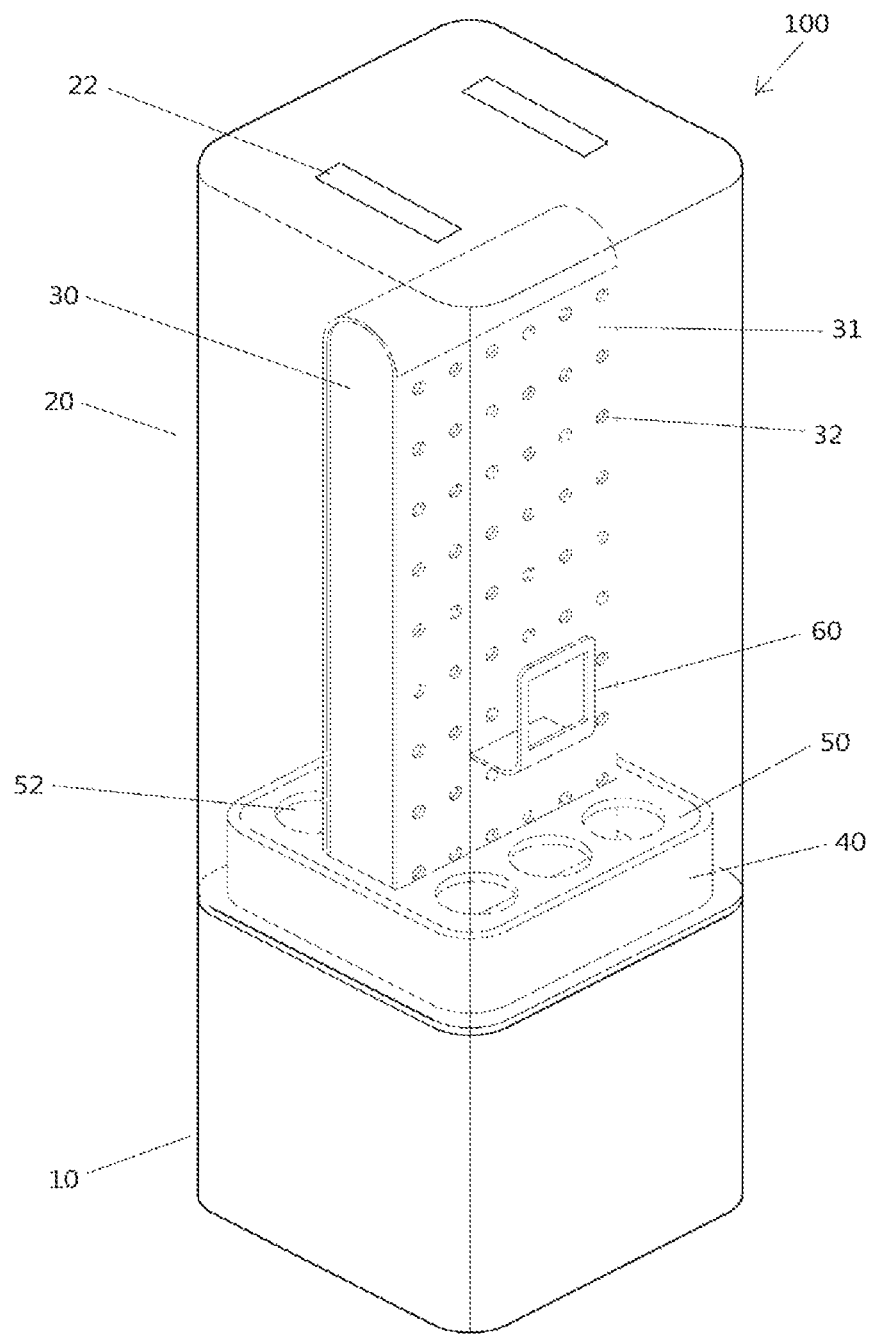
FIG. 1 is a perspective view of a sterilizer for toothbrushes, puffs for cosmetic use and cosmetic brushes according to the present invention.

FIG. 1 is a perspective view of a sterilizer for toothbrushes, puffs for cosmetic use and cosmetic brushes according to the present invention.

Figure 2:
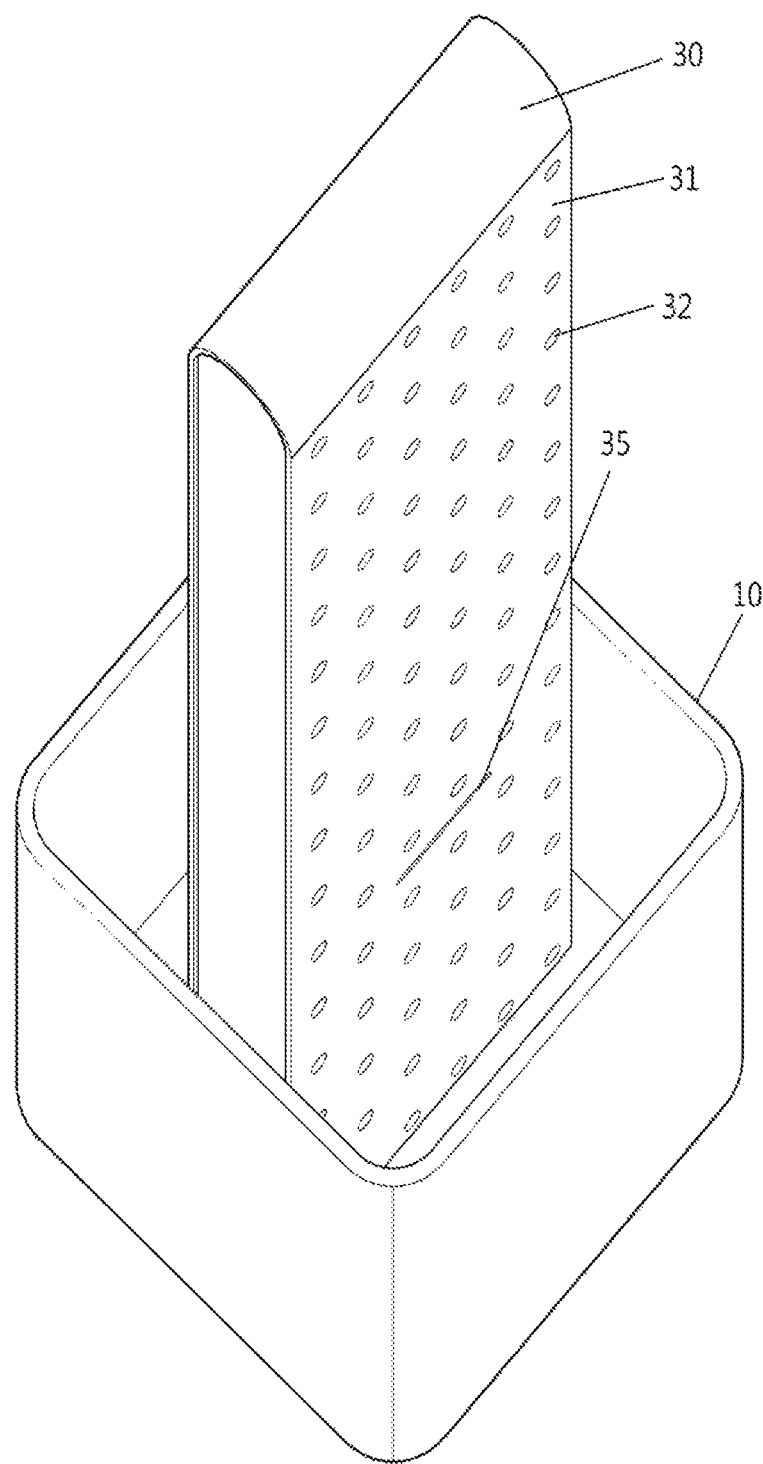
FIG. 2 is a perspective view of a housing and dehydrating sterilizer member of a sterilizer for toothbrushes, puffs for cosmetic use and cosmetic brushes according to the present invention.

FIG. 2 is a perspective view of a housing and dehydrating sterilizer member of a sterilizer for toothbrushes, puffs for cosmetic use and cosmetic brushes according to the present invention.

Figure 3A:
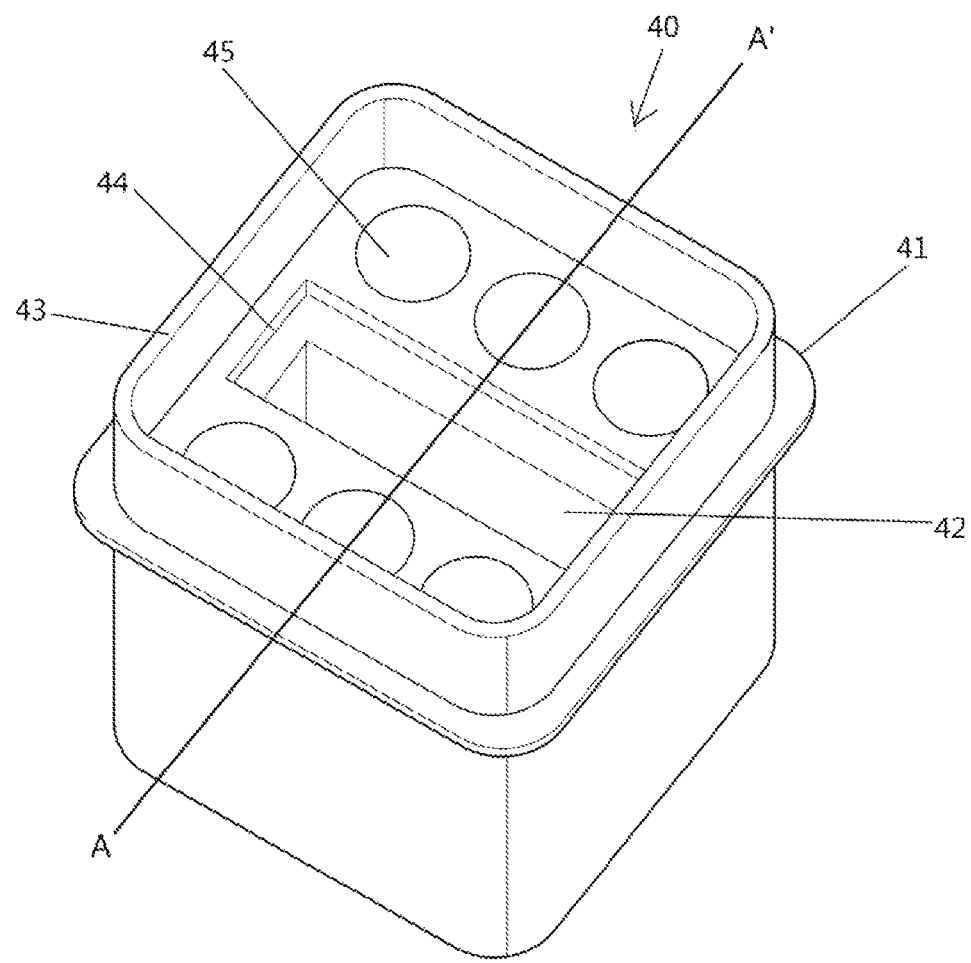
Figure 3B:
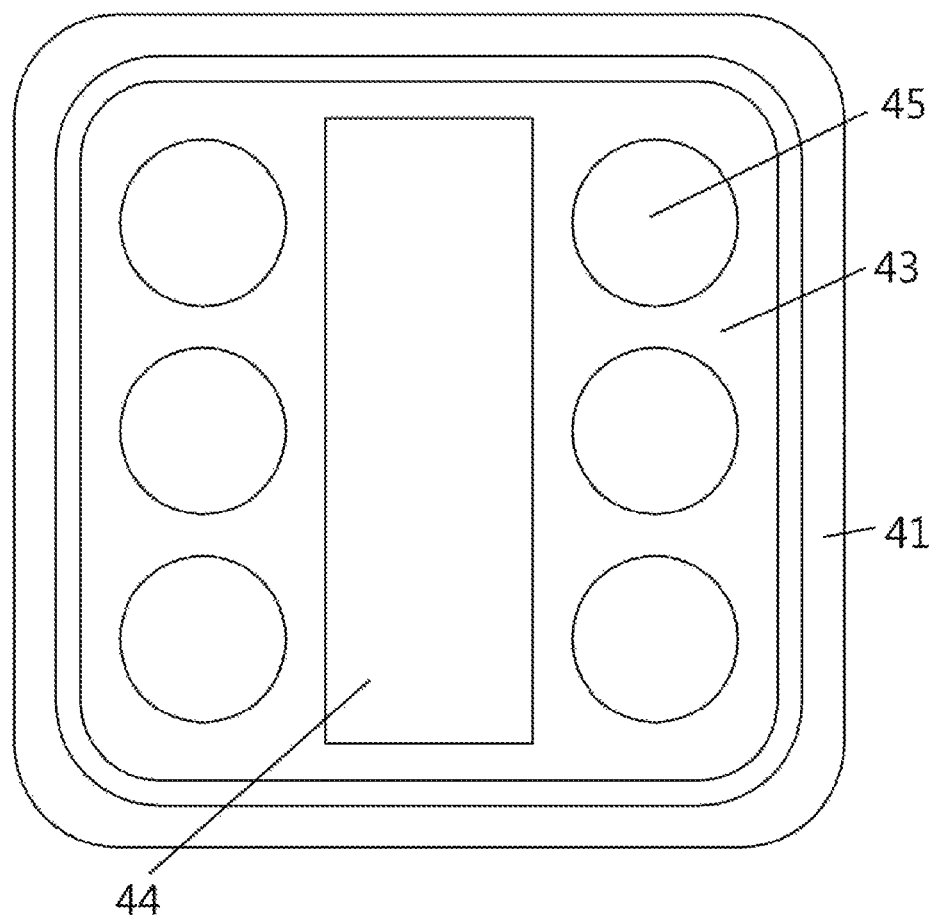
Figure 3C:
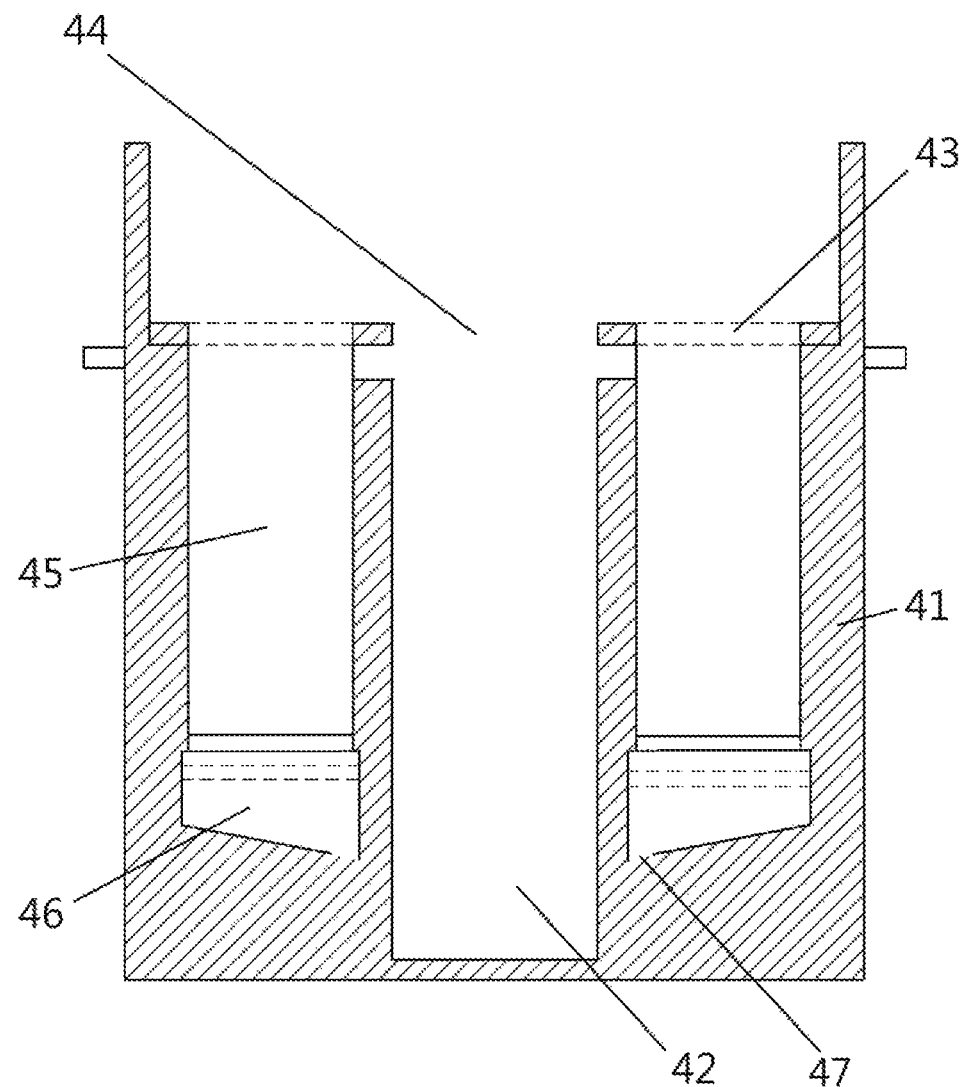
FIG. 3C is a cross-sectional view at A-A' of FIG. 3A.

FIG. 3A is a perspective view of a lower holder member and FIG. 3B is a top view of the lower holder member according to a sterilizer for toothbrushes, puffs for cosmetic use and cosmetic brushes according to the present invention while FIG. 3C is a cross-sectional view at A-A' of FIG. 3A.

Figure 4:
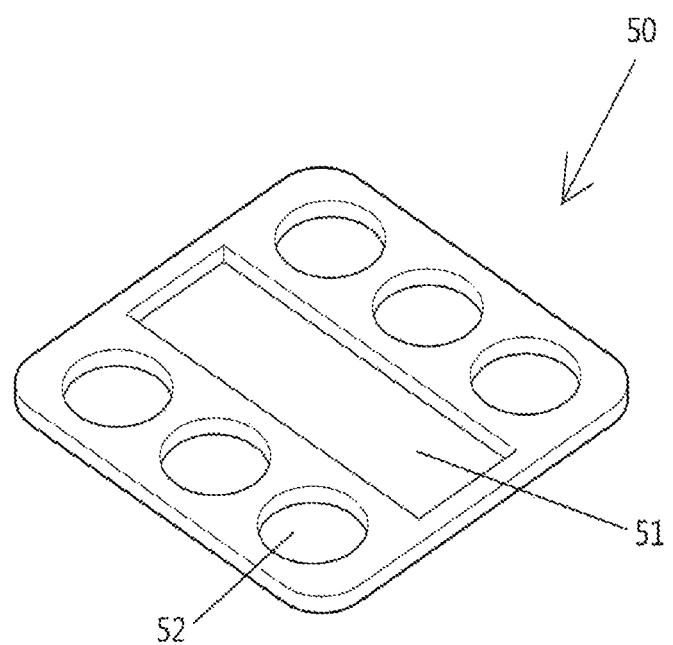
FIG. 4 is a perspective view of an upper holder member of a sterilizer for toothbrushes, puffs for cosmetic use and cosmetic brushes according to the present invention.

FIG. 4 is a perspective view of an upper holder member of a sterilizer for toothbrushes, puffs for cosmetic use and cosmetic brushes according to the present invention.

Figure 5:
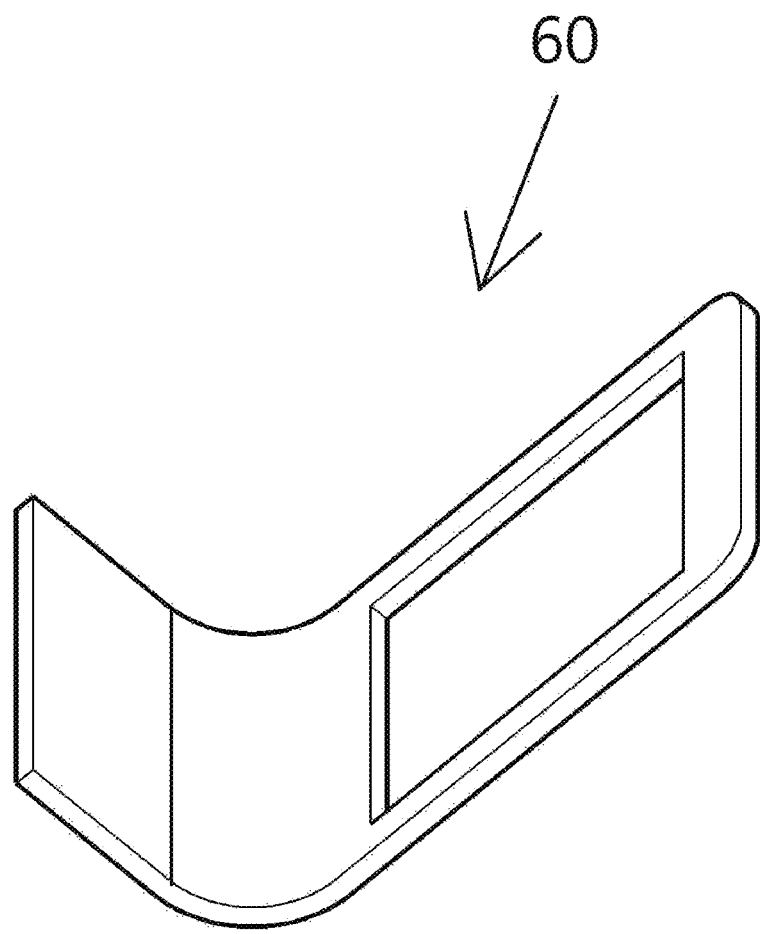
FIG. 5 is a perspective view of a holder of a sterilizer for toothbrushes, puffs for cosmetic use and cosmetic brushes according to the present invention.

FIG. 5 is a perspective view of a holder of a sterilizer for toothbrushes, puffs for cosmetic use and cosmetic brushes according to the present invention.

A sterilizer for toothbrushes, puffs for cosmetic use and cosmetic brushes 100 according to the present invention includes a housing 10 that assumes the shape of a hexahedron and has a certain size of an opening in the upper portion of the housing and an internal storage space, a cover 20 that assumes the shape of a hexahedron and has an opening in the lower portion of the cover so that the cover is laid on and removed from the housing 10 from above and an internal storage space, a dehydrating sterilizer member 30 that assumes the shape of a hollow panel with a certain width and thickness and protrudes vertically upwards from the center of the bottom surface of the housing, a lower holder member 40 that includes a first lower holder member 41 that is a hexahedron, to be inserted into the housing 10, with the top surface is open and has a insertion tube 42 that extends upwards from the bottom surface of the first lower holder member 41 so that the dehydrating sterilizer member 30 is inserted from above to the bottom surface of the first lower holder member 41 and a second lower holder member 43, to be inserted into the first lower holder member 41, that has a insertion hole 44 in the center of the top surface to accept the dehydrating sterilizer member 30 and two or more hole cups 45 in either longitudinal side of the insertion hole 44 that are hollowed downwards to accept a toothbrush and cosmetic brush, an upper holder member 50 that is a plate the shape of which is identical to the top surface of the second lower holder member 43 and placed on the upper portion of the lower holder member 40, and a holder 60 that is inserted into a slit 35 formed in a side of the dehydrating sterilizer member 30, thereby holding a puff for cosmetic use.

The cover 20 may be required to be made of transparent synthetic resin in order to see through the inside of the sterilizer for toothbrushes, puffs for cosmetic use and cosmetic brushes 100.

The dehydrating sterilizer member 30 has on the surface a heat radiating plate 31 that has a certain width and spreads out on front and rear side of the dehydrating sterilizer member 30 down to the bottom surface of the housing 10 while a plurality of negative ion emitting perforations 32 that penetrate at an identical interval the surface of the dehydrating sterilizer member 30 and the heat radiating plate 31 so that the heat radiating plate 31 exerts heat and, simultaneously, the negative ion emitting perforations 32 that penetrate the heat radiating plate 31 discharge negative ions.

The dehydrating sterilizer member 30 is equipped in the inside with a PTC heater 33 (not illustrated) that heats the heat radiating plate 31 in order to maintain the heat radiating plate 31 at 40 to 45° C., a range of temperature one may not think very hot when he or she touches his or her hand on the heat radiating plate, and a negative ion generator 34 (not illustrated) that generates negative ions.

The first lower holder member 41 has in the internal wall, at a certain height, a protuberance and the second lower holder member 43 has in the rim of the top surface a stumbling block in order to assemble the second lower holder member 43 with the first lower holder member 41 while the second lower holder member 43 is mounted to and demounted from the first lower holder member 41.

The first lower holder member 41 is not integrated, to be a single unit, with but capable of being demounted from the second lower holder member 43 in order for the first lower holder member 41 and the second lower holder member 43 to be separated from each other, thereby being washed out with ease.

The hole cup 45 of the second lower holder member 43 as a hollow cylinder having the top and bottom ends open has threads on the external surface of the lower end while a hole cup bottom lid member 46 as a hollow cylinder having the top end open has threads on the internal surface of the upper end so that the hole cup 45 and the hole cup bottom lid member 46 are fastened to and unfastened from each other.

The hole cup 45 is not integrated, to be a single unit, with but capable of being unfastened from the hole cup bottom lid member 46 in order for the hole cup 45 and the hole cup bottom lid member 46 to be separated from each other, thereby being washed out with ease because it is not convenient to cleanse any scale, etc. formed on the bottom surface of the hole cup 45 when the hole cup 45 and the hole cup bottom lid member 46 are manufactured into a single unit although the hole cup 45 and the hole cup bottom lid member 46 that are manufactured separable from each other render each of the hole cup 45 and the hole cup bottom lid member 46 conveniently washed out.

The bottom surface of the hole cup bottom lid member 46 has a clearance between the bottom surface of the first lower holder member 41 and is slanted to a slight extent while the low end of the bottom surface of the hole cup bottom lid member 46 has a crack 47 to drain water.

Such a configuration of the hole cup bottom lid member 46 draws the water that drops from a toothbrush after use and puff for cosmetic use and cosmetic brush after wash down to the bottom surface of the first lower holder member 41, not pooling on the bottom surface of the hole cup bottom lid member 46.

Any water pooled on the bottom surface of the first lower holder member 41 may be readily evaporated because such water has a wide area that contact air and the heat radiating plate 31 extends down to the center of the bottom surface of the housing 10 although the water, dropping from a toothbrush after use and puff for cosmetic use and cosmetic brush after wash then flowing down to the bottom surface of the hole cup 45, that is pooled on the bottom surface of the hole cup bottom lid member 46 may cause microbial proliferation and fungi growth, etc. on the handle of those toothbrushes and cosmetic brushes that contact the pooled water.

The upper holder member 50 has in the center an upper insertion hole 51 into which the dehydrating sterilizer member 30 is inserted and in either longitudinal side two or more upper hole cups 52.

The lower holder member 40 is provided separately from the upper holder member 50 in order to first, install the lower holder member 40, thereby stably holding the lower portion of a toothbrush and cosmetic brush inside the hole cups 45 of the second lower holder member 43 because those toothbrushes and cosmetic brushes that are accepted upright in the upper hole cups 52 may not be held stably in the lower portion of the toothbrushes and makeup brushes when only the upper holder member 50 is installed without the lower holder member 40; second, pull the lower holder member 40 and upper holder member 50 out of the housing 10 just easily and manually for cleansing because it may not be convenient to wash out the hole cups 45, etc. when the lower holder member 40 and upper holder member 50 are integrated with each other into a single unit; and third, manufacture the upper holder member 50, which is what a user mostly observes when seeing through the cover 20 the inside of the sterilizer for toothbrushes, puffs for cosmetic use and cosmetic brushes 100, out of quality materials but the lower holder member 40 out of lower-priced materials, thereby lowering the production costs.

The holder 60 that is inserted into the slit 35 formed in a side of the dehydrating sterilizer member 30, thereby holding a puff for cosmetic use is pulled out of the slit 35 for washing out with ease.

It may be required that the cover 20 have two or more protrusions 21 (not illustrated) in the internal surface so that the negative ions emitted via the negative ion emitting perforations 32 collide with the protrusions on the internal surface of the cover 20, thereby being dispersed in various directions.

Meanwhile, the cover 20 has two or more air vents 22 in the top surface, where air flows, when the cover 20 is open, into the sterilizer for toothbrushes, puffs for cosmetic use and cosmetic brushes 100 is heated by the heat radiating plate 31 radiates and the heated air rises upwards to be discharged off the air vents 22 formed in the top surface of the cover 20, thereby generating an air flow that rises upwards from the lower portion of the sterilizer 100 then discharging, without an independently provided exhaust fan, the air that contains the moisture evaporated from the water drawn to and pooled on the bottom surface of the first lower holder member 41.

In general, a toothbrush is held, regardless of whether it is long or short, in the hole cup 45 and the upper hole cup 52, where the brush portion may face the heat radiating plate 31 and the negative ion emitting perforations 32, or not, when it is inserted in the hole cup 45 and the upper hole cup 52 without paying attention to direction.

Likewise, a puff for cosmetic use is held, in general, in the holder 60, where the face-touching surface of the puff for cosmetic use may face the heat radiating plate 31 and the negative ion emitting perforations 32, or not, when it is inserted in the holder 60 without paying attention to direction.

The heat radiating plate 31 has a certain width and spreads out on front and rear side of the dehydrating sterilizer 30 down to the bottom surface of the housing 10 while the plurality of negative ion emitting perforations 32 penetrate at an identical interval the heat radiating plate 31, which makes each toothbrush or cosmetic brush dehydrated and sterilized in an identical way regardless of its length.

Provided that a user neither brushes his or her teeth nor puts on makeup very frequently in a short period of time, each of those toothbrushes and puffs for cosmetic use that are exposed to the heat radiating plate 31 and the negative ion emitting perforations 32 is dehydrated and sterilized regardless of direction.

In particular, according to the present invention, unlike prior art, a user may be convenient because he or she needs not make sure that a toothbrush or puff for cosmetic use to be held faces the heat radiating plate 31 and the negative ion emitting perforations 32.

The sterilizer for toothbrushes, puffs for cosmetic use and cosmetic brushes 100 according to the present invention becomes ready to use by putting down the first lower holder member 41 from above and through the dehydrating sterilizer member 30 then plugging the first lower holder member 41 in the housing 10, inserting the second lower holder member 43 in the first lower holder member 41, placing the upper holder member 50 on the second lower holder member 43, inserting a toothbrush, puff for cosmetic use and cosmetic brush in the hole cup 45, the upper hole cup 52 and the holder 60 and finally covering the housing 10 with the cover 20.

A toothbrush, puff for cosmetic use and cosmetic brush that is held in the hole cup 43, upper hole cup 52 and holder 60, respectively, is dehydrated and sterilized by heating the heat radiating plate 41 with the PTC heater 33 and emitting negative ions via the negative ion emitting perforations 32 from the negative ion generator 34 when supplying electric power by making a power switch (not illustrated) of the sterilizer for toothbrush, puffs for cosmetic use and cosmetic brushes 100 according to the present invention.

For washing out the sterilizer for toothbrush, puffs for cosmetic use and cosmetic brushes 100 according to the present invention, a user may remove the cover 20 and pull out the upper holder member 50, second lower holder member 43 and first lower holder member 41 one after another then cleanse the members.

The sterilizer for toothbrush, puffs for cosmetic use and cosmetic brushes 100 according to the present invention may lower the production costs by dividing the lower holder member 40 from the upper holder member 50, thereby manufacturing the lower holder member 40 out of low-priced materials, omitting an independent toothbrush holder, etc. that would otherwise be installed for arranging the brush portion of a toothbrush in a predetermined direction, also omitting an exhaust fan that exhausts the air contained in the sterilizer for toothbrush, puffs for cosmetic use and cosmetic brushes 100, etc., which otherwise would increase the production costs and potentially incur failures in the exhaust fan, noise in operating the fan, electric power consumption to operate the fan, etc.

The sterilizer for toothbrush, puffs for cosmetic use and cosmetic brushes 100 according to the present invention may be problemproof and lower the production costs because the sterilizer for toothbrush, puffs for cosmetic use and cosmetic brushes 100 according to the present invention is operated only by making the power switch, without installing an independent control circuit that renders the device power-on by putting on the cover 20 and vice versa as found in common in prior art.

REFERENCE NUMERALS

100: Sterilizer for toothbrush, puffs for cosmetic use and cosmetic brushes according to the present invention

10: Housing
20: Cover
21: Protrusion
22: Air vent
30: Dehydrating sterilizer member
31: Heat radiating plate
32: Negative ion emitting perforation
33: PTC heater
34: Negative ion generator
35: Slit
40: Lower holder member
41: First lower holder member
42: insertion tube
43: Second lower holder member
44: insertion hole
45: Hole cup
46: Hole cup bottom lid member
47: Crack
50: Upper holder member
51: Upper insertion hole
52: Upper hole cup
60: Holder

What is claimed is:

1. A sterilizer for toothbrushes, puffs for cosmetic use and cosmetic brushes including:

a housing (10) that assumes the shape of a hexahedron and has a certain size of an opening in the upper portion of the housing and an internal storage space;

a cover (20) that assumes the shape of a hexahedron and has an opening in the lower portion of the cover so that the cover is laid on and removed from the housing (10) from above and an internal storage space;

a dehydrating sterilizer member (30) that assumes the shape of a hollow panel with a certain width and thickness and protrudes vertically upwards from the center of the bottom surface of the housing;

a lower holder member (40) that includes a first lower holder member (41) that is a hexahedron, to be inserted into the housing (10), with the top surface is open and has a insertion tube (42) that extends upwards from the bottom surface of the first lower holder member (41) so that the dehydrating sterilizer member (30) is inserted from above to the bottom surface of the first lower holder member (41) and a second lower holder member (43), to be inserted into the first lower holder member (41), that has an insertion hole (44) in the center of the top surface to accept the dehydrating sterilizer member (30) and two or more hole cups (45) in either longitudinal side of the insertion hole (44) that are hollowed downwards to accept a toothbrush and cosmetic brush;

an upper holder member (50) that is a plate the shape of which is identical to the top surface of the second lower holder member (43) and placed on the upper portion of the lower holder member (40); and a holder (60) that is inserted into a slit (35) formed in a side of the dehydrating sterilizer member (30), thereby holding a puff for cosmetic use.

2. The sterilizer for toothbrushes, puffs for cosmetic use and cosmetic brushes of claim 1, wherein the dehydrating sterilizer member (30) has on the surface a heat radiating plate (31) that has a certain width and spreads out on front and rear side of the dehydrating sterilizer member (30) down to the bottom surface of the housing (10) while a plurality of negative ion emitting perforations (32) that penetrate at an identical interval the surface of the dehydrating sterilizer member (30) and the heat radiating plate (31) so that the heat radiating plate (31) exerts heat and, simultaneously, the negative ion emitting perforations (32) that penetrate the heat radiating plate discharge negative ions.

3. The sterilizer for toothbrushes, puffs for cosmetic use and cosmetic brushes of claim 1, wherein the first lower holder member (41) has in the internal wall, at a certain height, a protuberance and the second lower holder member (43) has in the rim of the top surface a stumbling block in order to assemble the second lower holder member (43) with the first lower holder member (41) while the second lower holder member (43) is mounted to and demounted from the first lower holder member (41).

4. The sterilizer for toothbrushes, puffs for cosmetic use and cosmetic brushes of claim 1, wherein the hole cup (45) of the second lower holder member (43) as a hollow cylinder having the top and bottom ends open has threads on the external surface of the lower end while a hole cup bottom lid member (46) as a hollow cylinder having the top end open has threads on the internal surface of the upper end so that the hole cup (45) and the hole cup bottom lid member (46) are fastened to and unfastened from each other.

5. The sterilizer for toothbrushes, puffs for cosmetic use and cosmetic brushes of claim 4, wherein the hole cup (45) and the hole cup bottom lid member (46) are disassembled from each other in order to wash out with ease the hole cup (45) and the hole cup bottom lid member (46).

6. The sterilizer for toothbrushes, puffs for cosmetic use and cosmetic brushes of claim 4, wherein the bottom surface of the hole cup bottom lid member (46) has a clearance between the bottom surface of the first lower holder member (41) and is slanted to a slight extent while the low end of the bottom surface of the hole cup bottom lid member (46) has a crack (47) to drain water.

7. The sterilizer for toothbrushes, puffs for cosmetic use and cosmetic brushes of claim 1, wherein the upper holder member (50) has in the center an upper insertion hole (51) into which the dehydrating sterilizer member (30) is inserted and in either longitudinal side two or more upper hole cups (52).

8. The sterilizer for toothbrushes, puffs for cosmetic use and cosmetic brushes of claim 1, wherein both the lower holder member (40) and the upper holder member (50) are be pulled out of the housing (10) by simply and manually drawing them for cleansing with ease while the holder (60) is pulled out of the slit (35) for cleansing with ease.

9. The sterilizer for toothbrushes, puffs for cosmetic use and cosmetic brushes of claim 1, wherein the cover (20) has two or more protrusions in the internal surface so that the negative ions emitted via the negative ion emitting perforations (32) collide with the protrusions on the internal surface of the cover, thereby being dispersed in various directions.

10. The sterilizer for toothbrushes, puffs for cosmetic use and cosmetic brushes of claim 1, wherein the cover (20) has two or more air vents (22) in the top surface.

\* \* \* \* \*